(12) United States Patent
Wen

(10) Patent No.: US 7,156,897 B2
(45) Date of Patent: Jan. 2, 2007

(54) ANTI-INFECTION AND TOXIN ELIMINATION DEVICE

(76) Inventor: Sheree H. Wen, 796 Longhill Rd. West, Briarcliff Manor, NY (US) 10510

( * ) Notice: Subject to any disclaimer, the term of this patent is extended or adjusted under 35 U.S.C. 154(b) by 196 days.

(21) Appl. No.: 10/433,676

(22) PCT Filed: Feb. 14, 2003

(86) PCT No.: PCT/US03/04514

§ 371 (c)(1),
(2), (4) Date: Jun. 9, 2004

(87) PCT Pub. No.: WO03/078571

PCT Pub. Date: Sep. 25, 2003

(65) Prior Publication Data

US 2004/0231696 A1    Nov. 25, 2004

Related U.S. Application Data

(63) Continuation-in-part of application No. 09/996,861, filed on Nov. 27, 2001, now Pat. No. 6,673,137.

(60) Provisional application No. 60/357,335, filed on Feb. 14, 2002.

(51) Int. Cl.
*B03C 1/02* (2006.01)
*B03C 3/016* (2006.01)

(52) U.S. Cl. ............... 95/28; 55/385.2; 95/58; 95/70; 96/3; 96/16; 96/18; 96/55; 96/224; 422/24; 422/121

(58) Field of Classification Search .......... 96/2, 96/3, 15–26, 55–63, 74, 224; 95/2–4, 25, 95/28, 58, 69, 70; 134/1, 1.3; 588/301; 422/186, 186.21, 186.23, 24, 121; 55/385.2
See application file for complete search history.

(56) References Cited

U.S. PATENT DOCUMENTS

| 1,891,256 | A | | 12/1932 | Bilde | .................... 96/222 |
| 3,230,033 | A | | 1/1966 | Hamilton et al. | ........... 422/121 |
| 3,478,758 | A | | 11/1969 | Davies | ..................... 134/8.5 |
| 3,804,942 | A | * | 4/1974 | Kato et al. | ............... 423/239.1 |
| 3,817,703 | A | | 6/1974 | Atwood | ..................... 422/22 |

(Continued)

FOREIGN PATENT DOCUMENTS

DE            3739979 A1      6/1989

(Continued)

*Primary Examiner*—Richard L. Chiesa
(74) *Attorney, Agent, or Firm*—Robert D. Katz, Esq.; Cooper & Dunham LLP

(57) ABSTRACT

The invention provides an apparatus for removing airborne pathogens and toxic substances from a surface of an article or a volume of air, comprising: a main processing chamber having a door for ingress to and egress from the main processing chamber, at least two high voltage electrodes for generating a current. The electrode can form ozone, if desired, to destroy pathogens. Optionally, the electrodes can be in a sealed or unsealed glass tube, with or without mercury, to generate ultraviolet light for photochemical reaction with pathogens or other contaminants. The apparatus also includes a post processing chamber comprising at least one filter for removing or absorbing airborne particulates and pathogens, and includes low voltage electrodes to neutralize charges in air transmitted from the main processing chamber. The system further includes a shutter between the main processing chamber and the post processing chamber for preventing ultraviolet light from entering the post processing chamber from the main processing chamber; and a fan for moving fluid from the main processing chamber to the post processing chamber.

16 Claims, 3 Drawing Sheets

U.S. PATENT DOCUMENTS

| | | | |
|---|---|---|---|
| 3,915,180 A | 10/1975 | Jacobs | 134/58 D |
| 3,926,556 A | 12/1975 | Boucher | 422/21 |
| 4,102,654 A * | 7/1978 | Pellin | 96/16 |
| 4,203,948 A * | 5/1980 | Brundbjerg | 422/121 |
| 4,207,286 A | 6/1980 | Gut Boucher | 422/21 |
| 4,431,612 A * | 2/1984 | Bell et al. | 422/186.21 |
| 4,468,372 A | 8/1984 | Seifert et al. | 96/52 |
| 4,513,470 A | 4/1985 | Toya | 15/328 |
| 4,536,914 A | 8/1985 | Levine | 15/344 |
| 4,542,557 A | 9/1985 | Levine | 15/344 |
| 4,574,714 A * | 3/1986 | Bach et al. | 588/314 |
| 4,577,365 A | 3/1986 | Yuen | 15/339 |
| 4,591,485 A | 5/1986 | Olsen et al. | 422/20 |
| 4,610,048 A | 9/1986 | Ishihara et al. | 15/344 |
| 4,836,684 A | 6/1989 | Javorik et al. | 366/114 |
| 4,876,852 A * | 10/1989 | Abthoff et al. | 60/275 |
| 4,924,548 A | 5/1990 | Touya et al. | 15/347 |
| 5,120,499 A | 6/1992 | Baron | 422/24 |
| 5,244,629 A | 9/1993 | Caputo et al. | 422/22 |
| 5,320,805 A | 6/1994 | Kramer et al. | 422/28 |
| 5,364,645 A | 11/1994 | Lagunas-Solar et al. | 426/248 |
| 5,492,882 A | 2/1996 | Doughty et al. | 502/417 |
| 5,589,396 A | 12/1996 | Frye et al. | 436/73 |
| 5,593,476 A | 1/1997 | Coppom | 95/78 |
| 5,647,890 A | 7/1997 | Yamamoto | 95/69 |
| 5,651,811 A | 7/1997 | Frey et al. | 96/69 |
| 5,656,063 A | 8/1997 | Hsu | 95/58 |
| 5,711,017 A * | 1/1998 | Bitler et al. | 588/311 |
| 5,725,623 A | 3/1998 | Bowerman et al. | 55/490 |
| 5,779,769 A | 7/1998 | Jiang | 96/55 |
| 5,837,040 A * | 11/1998 | Caughron et al. | 96/224 |
| 5,927,304 A | 7/1999 | Wen | 134/153 |
| 5,944,873 A | 8/1999 | Jager et al. | 95/25 |
| 6,029,712 A | 2/2000 | Dougherty | 138/141 |
| 6,056,808 A | 5/2000 | Krause | 96/24 |
| 6,063,170 A | 5/2000 | Deibert | 96/224 |
| 6,094,775 A | 8/2000 | Behmer | 15/329 |
| 6,171,375 B1 | 1/2001 | Howie | 96/17 |
| 6,190,437 B1 | 2/2001 | Forsyth | 95/90 |
| 6,203,600 B1 | 3/2001 | Loreth | 96/40 |
| 6,221,314 B1 * | 4/2001 | Bigelow | 422/24 |
| 6,245,132 B1 * | 6/2001 | Feldman et al. | 96/28 |
| 6,295,692 B1 | 10/2001 | Shideler | 15/327.5 |
| 6,296,692 B1 | 10/2001 | Gutmann | 96/62 |
| 6,333,004 B1 | 12/2001 | Sheldon | 422/4 |
| 6,379,427 B1 * | 4/2002 | Siess | 95/57 |
| 6,434,785 B1 | 8/2002 | Vandenbelt et al. | 15/344 |
| 6,468,433 B1 | 10/2002 | Tribelski | 210/748 |
| 6,673,137 B1 * | 1/2004 | Wen | 96/224 |
| 2001/0043887 A1 | 11/2001 | Morneault et al. | 422/121 |
| 2003/0010211 A1* | 1/2003 | Yu | 96/16 |

FOREIGN PATENT DOCUMENTS

| | | | |
|---|---|---|---|
| FR | 2599255 | | 12/1987 |
| GB | 947699 | | 1/1964 |
| GB | 2162424 | | 2/1986 |
| JP | 62-282686 | | 12/1987 |
| JP | 63-100955 | * | 5/1988 |
| JP | 2-43984 | | 2/1990 |

* cited by examiner

ANTI-INFECTION AND TOXIN ELIMINATION DEVICE

CROSS-REFERENCE RELATED APPLICATIONS

This is a national stage application under 35 U.S.C. §371 of International Application No. PCT/2003/004514 filed on Feb. 14, 2003. This application is a continuation-in-part of U.S. patent application Ser. No. 09/996,861, filed on Nov. 27, 2001, now U.S. Pat. No. 6,673,137, and claims the benefit of U.S. Provisional Patent Application No. 60/357,335, filed on Feb. 14, 2002.

FIELD OF THE INVENTION

This invention relates to devices that eliminate harmful airborne bacteria, viruses, and other disease vectors, as well as toxic substances, including pesticides, toxins and poisons, and more particularly to a device that may be used to remove pathogens and toxic substances from the air, the food and water supply, and from solid surfaces, including utensils, tools, walls, carpet, toys, furniture, and other household articles.

BACKGROUND OF THE INVENTION

Various devices and approaches have been developed to treat food products that may have been exposed to disease producing bacteria, viruses, spores and other vectors, and to neutralize or remove harmful chemicals, including toxins, pesticides, or other substances that may have been applied to food items, such as meat, fish, fruits and vegetables, and dairy products.

U.S. Pat. No. 5,927,304 (Wen) discloses a food article washer that includes a container for holding food articles, such as fruits and vegetables, and an ultrasonic generator to loosen dirt and debris from the surface of the food, and to provide agitation to the cleaning liquid to help remove insecticides and other possibly toxic substances thereon. The food article washer also includes an ultraviolet light generator to kill pathogens inhabiting the food surface, including disease-causing bacteria, viruses, spores and protozoa.

Others have discussed air purifiers or filters to remove airborne disease pathogens, as well as to neutralize toxic substances in the air. U.S. Pat. Nos. 5,647,890 (Yamamoto); 5,779,769 (Jiang); 6,296,692 (Gutmann); 6,203,600 (Loreth); 5,656,063 (Hsu); and U.S. Published Patent Application No. 20010043887 (Mornecult) disclose various types of air purifiers. They appear to use a combination of techniques to remove air impurities. In several of the systems, ionization removes airborne particulates, such as dirt, dust, smoke, asbestos, and other solid dry particles. An ozone source present in some of the purifiers helps remove noxious odors and chemical contaminants, as well as airborne pathogens.

A need exists for an improved infection and toxin eliminating device. It is therefore an object of the invention to provide an infection and toxin elimination device, which can remove pathogens, insecticides and toxic substances from food articles, utensils, toys, clothing and other articles, substantially without damaging the item being treated.

SUMMARY OF THE INVENTION

The foregoing and other objects are achieved, and the disadvantages of prior devices overcome in accordance with the practice of the present invention. The invention provides a germicidal device that can be used on food, liquid, solid surfaces and/or air, without using a radioactive process. The device and the process do not harm or change the physical and chemical structure of the object.

The invention provides an apparatus for removing airborne pathogens and toxic substances from a surface of an article or a volume of air, comprising: a main processing chamber having a door for ingress to and egress from the main processing chamber, at least two high voltage electrodes for generating a current. The electrode can form ozone, if desired, to destroy pathogens. Optionally, the electrodes can be in a sealed or unsealed glass tube, with or without mercury, to generate ultraviolet light for photochemical reaction with pathogens or other contaminants. The apparatus also includes a post processing chamber comprising at least one filter for removing or absorbing airborne particulates and pathogens, and includes low voltage electrodes to neutralize charges in air transmitted from the main processing chamber. The system further includes a shutter between the main processing chamber and the post processing chamber for preventing ultraviolet light from entering the post processing chamber from the main processing chamber, and a fan for moving fluid from the main processing chamber to the post processing chamber.

The invention further provides a process for removing airborne pathogens and toxic substances from a surface of an article or a volume of air. In one embodiment, the process comprises introducing the article or volume of air into a main processing zone having a pair of high voltage electrodes, and an optional ozone source and an optional ultraviolet light source. The article or volume of air is exposed to the electric voltage from the high voltage electrodes, and optionally to ozone and ultraviolet light in the main processing zone for a period of time sufficient to kill pathogens, including bacteria, viruses, and spores, and to neutralize toxic substances or poisons on the article or in the volume of air. After that air is removed from the main processing zone to a post processing zone, and filtered to remove any pathogens or toxic substances remaining therein. The air is exposed to low voltage electrodes (less than about 100 volts) to neutralize ions in the air. Following that, the air is expelled from the post processing zone.

BRIEF DESCRIPTION OF THE DRAWINGS

Other advantages and features of the present invention can be understood by reviewing the following detailed description of the preferred embodiments taken in conjunction with the accompanying drawings in which.

DETAILED DESCRIPTION OF THE PREFERRED EMBODIMENT

Figure 1:
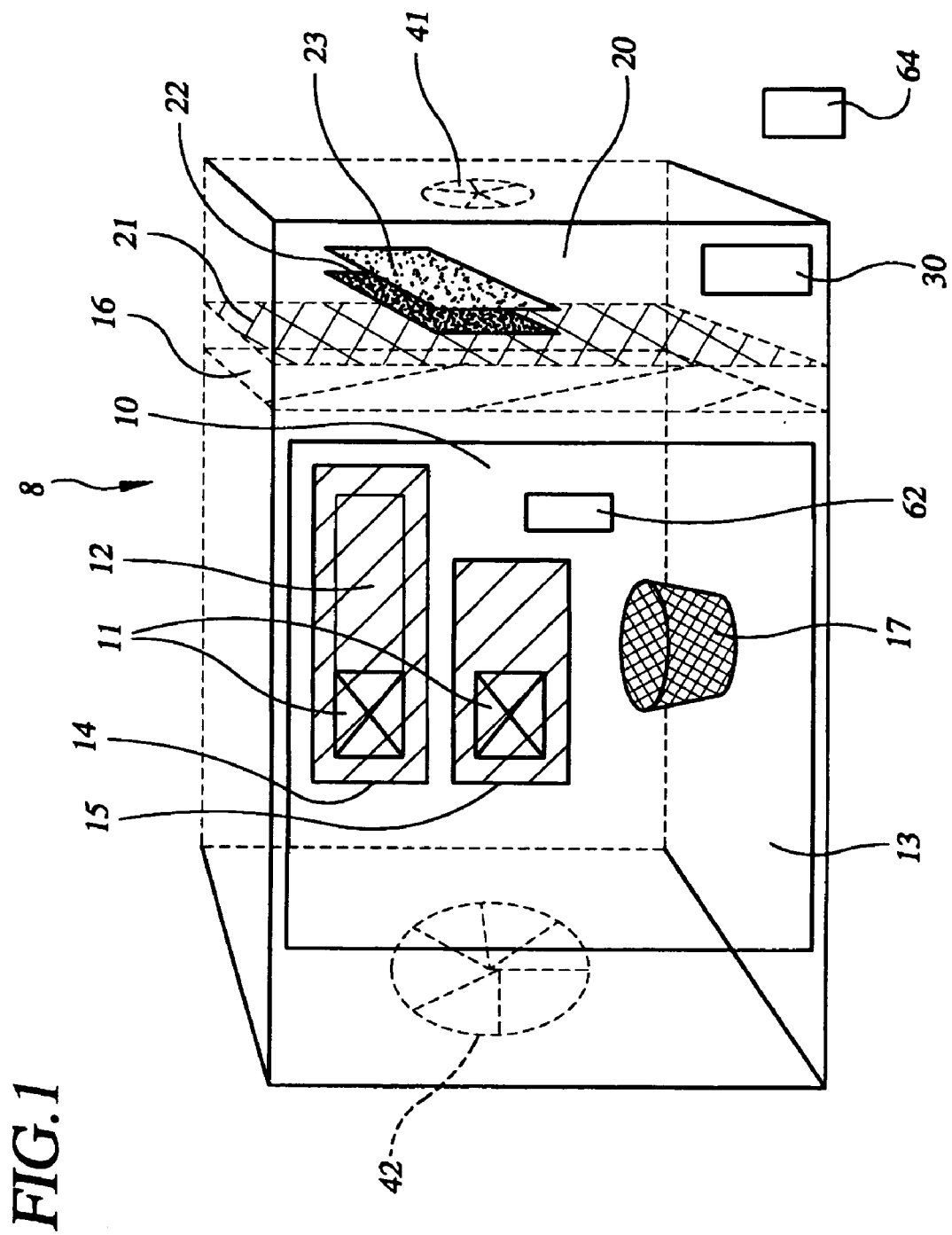
FIG. 1 is a schematic view of the infection and toxic elimination system of the present invention.

Referring to the drawings, FIG. 1 illustrates a preferred embodiment of the infection and toxin elimination system of the present invention, generally designated by the reference numeral 8. The system includes a main processing chamber 10, a post-processing chamber 20 and control electronics 30.

The main processing chamber 10 has two or more high voltage electrodes 11, which activate and ionize air, water, or other agents, and which generate reactants. The high voltage electrodes generate an electric and magnetic field sufficient to kill pathogens. The electrodes can also be used to generate ozone or generate UV light in the 200–400 nm range if placed in an enclosed glass 12. The glass 12 may be a sealed or unsealed tube, which may have a gas mixture including mercury vapor. An electromagnetic wave generator and/or microwave generator may also be included in the main process chamber 10. The main processing chamber 10 includes a door 13, which enables the placement of subjects such as food, drink (including milk), utensils and tools inside the chamber. A wire shelf or basket 17 sits inside the chamber to hold the subject articles, and to maximize reactive penetration of agents and UV radiation. A fan may help circulate air within the main processing chamber 10, and it may include an optional particulate filter.

A shutter 14 screens out UV radiation for certain processes, or screens out reactive air for other process components. Shutter 15 may be open or closed either manually or automatically for different articles and cleaning processes. Shutter 16 separates the main process chamber 10 and the post process chamber 20 during operation. The shutters open or close during the process to isolate activated agents, photons and/or other process components, as desired. Filters are placed between the main process chamber and post process chamber to retain particles of pathogens in the process chamber prior to and during the process of extracting harmful substances. The device has automatic safety switches for doors and shutters.

The post processing chamber 20 includes one or more fine grain passive filters 21 with or without electrostatic properties, to filter out large, unwanted particles or to retain large bacteria or spores in the chamber 20 during the operation of the process. Chamber 20 may also include metal filters to neutralize residual gas. The post process chamber 20 also includes low voltage electrodes 22, 23 in wire grids, perforated sheets or multiple sheets, preferably emitting voltage of less than about 100 volts. The activated, charged air in the post processing chamber 20 picks up electrons from electrodes 22 or releases electrons to the electrodes 22, and returns to a neutral state. The post-processing chamber 20 also has neutralization filters such as carbon filters or filters impregnated or fabricated with an absorbent material that further turns the residual gas into fresh air.

The system 8 has one or more fans 41 to draw the air or gas from the process chamber 10 through post process chamber 20 and then outside the system. The system 8 also optionally has a fan 42 at the inlet of main process chamber 10, to enable the system 8 to be used as an air cleaner to purify the surrounding air. As mentioned above, additional fans may be provided to improve circulation within the systems. The inlet fan 42 is also optionally equipped with a suction hose 51 that makes the device act as a vacuum cleaner that can clean the surface of rugs, carpet, furniture, machines, larger household articles, protective clothing of workers exposed to pathogens and toxic substances, and difficult to reach places.

The process alters ambient air and water properties to react with bacteria, viruses and poisonous or toxic substances. The process chamber of the device is comprised of plural high voltage electrodes in the range of 5 kv–100 kv. The discharge of high voltage electrodes alternate air and water and form energized, reactive species in reactive atomic, ionized or molecular form. One or more high voltage electrodes may be enclosed in glass with a filler gas, including mercury, to form an ultraviolet light source at approximately 200 nm–300 nm wavelength, as one of the sources for photochemical processes. Additional water and/or other liquids such as alcohol, hydroxyl, methanol, peroxide, salt, detergent, starch, soy, olive oil, chlorine and process enhancing chemicals, and enzyme containing solutions may also be injected through spray, vaporization or discharge to enhance process efficiency. The interior of the chamber is preferably made of or contains metals, such as Fe, Mo, V, Zn, or I in solid, ionic, or complex molecular form.

In another embodiment, wherein the system is scaled to enclose one or more persons, with or without their vehicles, the system 8 can act as a decontamination chamber, or be attached to a decontamination tent or chamber to remove airborne pathogens, toxic substances, and the like from persons exposed thereto. The protective garment on the subject person undergoing decontamination acts as a shield against ionized air and particles, ozone, UV exposure, and the other possibly hazardous substances used as decontaminants in the system 8.

Figure 2:
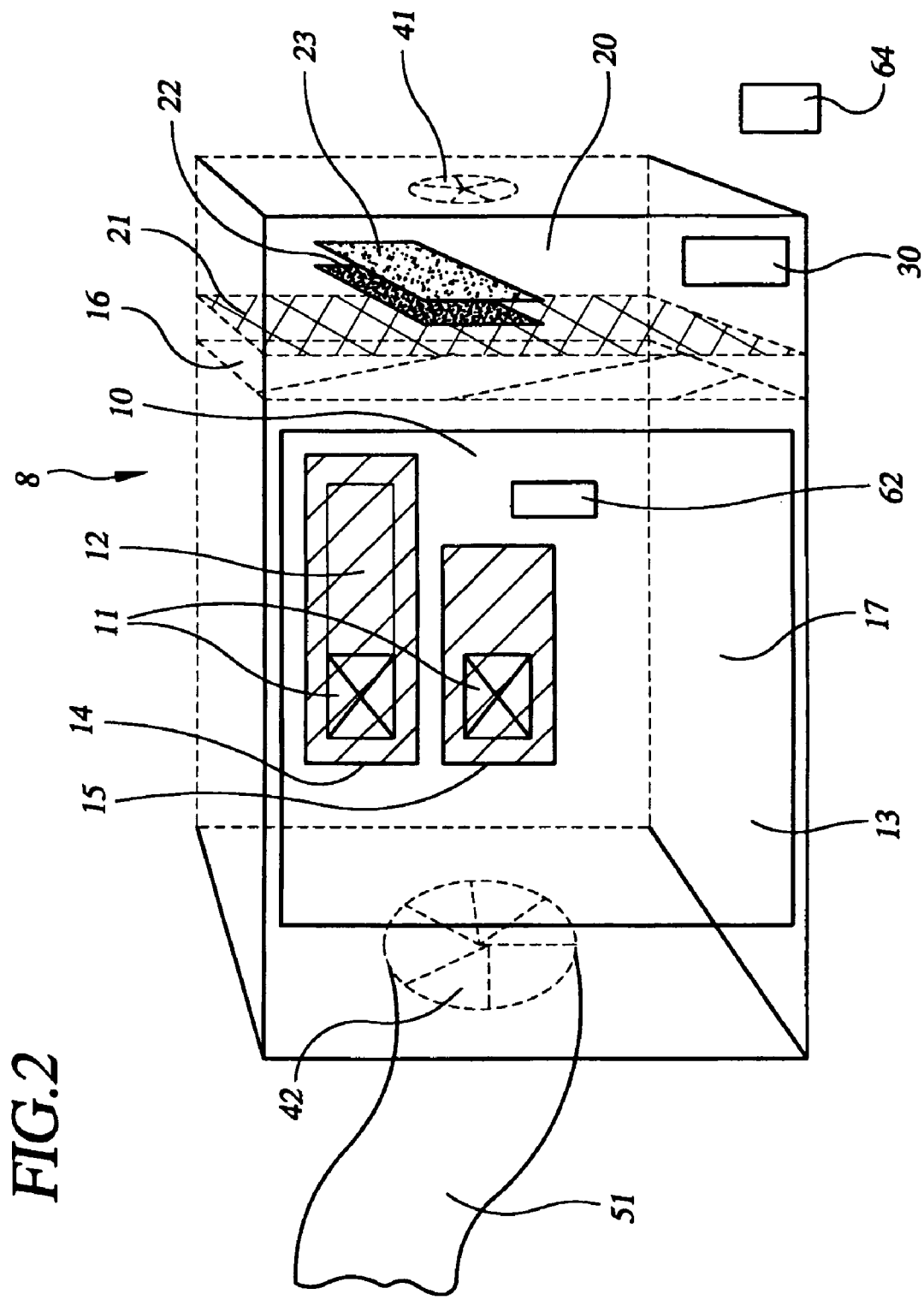
FIG. 2 is a schematic view of a second embodiment of the infection and toxin elimination system of the present invention.

By attaching hose 51 to fan 42 as shown in FIG. 2, the system 8 can also operate as an in situ cleaning device that delivers the reactive air to the interior of other machines or chambers to do the required cleaning. The arrangement in FIG. 2 can also be used to clean the bacteria or pathogens on a human or animal body as a medical device to promote healing of skin lesions, herpes or HIV, etc., however the disease was contracted.

Figure 3:
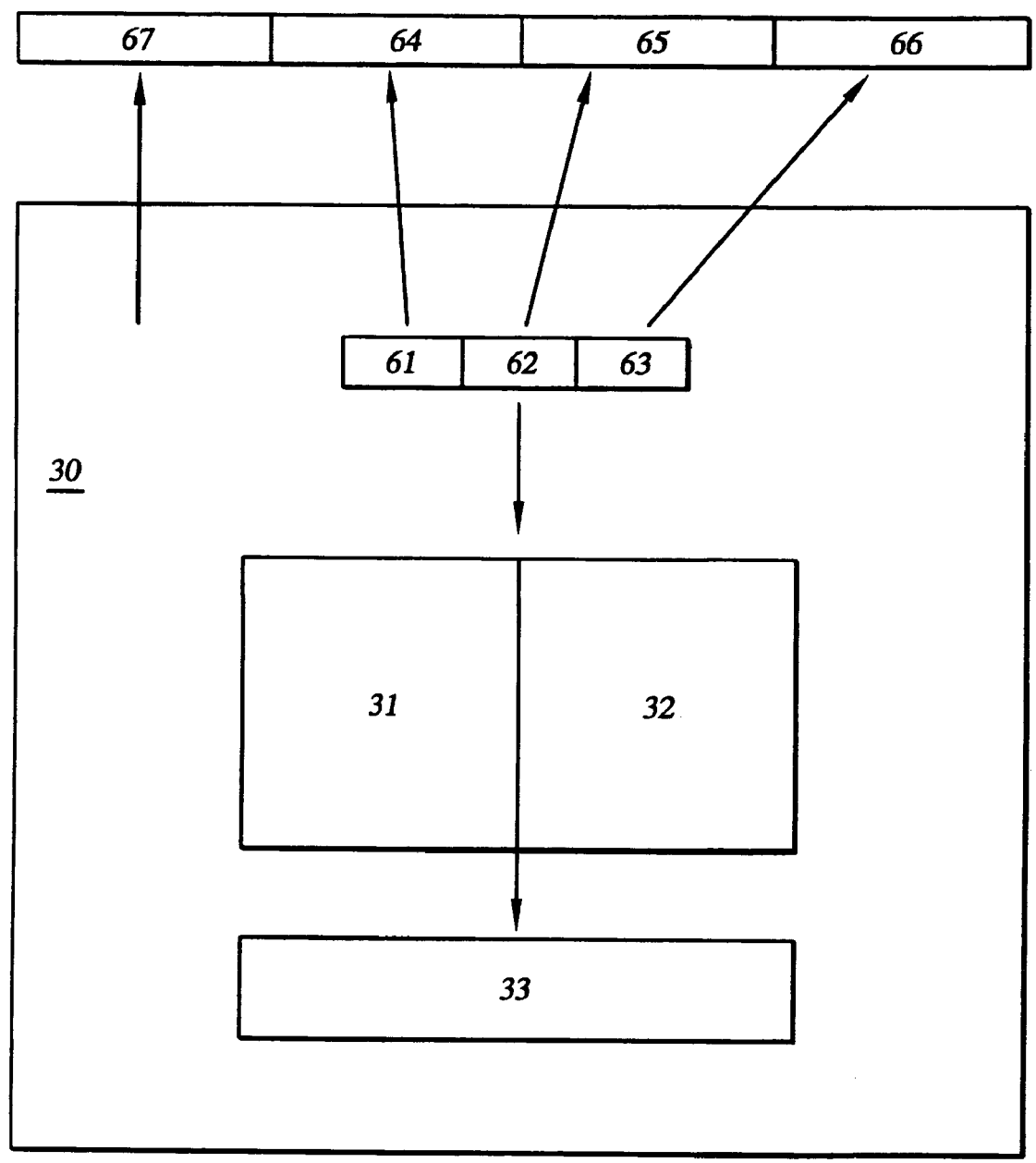
FIG. 3 is a block diagram of electronic control circuitry for the infection and toxin elimination system of the present invention.

The control electronics 30 described in FIG. 3 include a microprocessor 31 or dial electronics 32 to control all elements of the device 33 to function as the prescribed process, which may be stored in microprocessors and memory devices. The system 8 contains sensors 61, 62, 63 located within the processing chamber, post processing chamber and outside of the system. The sensors 61, 62, 63 are connected to the control electronics 30, recording device 64, at least one computer 65, microprocessors 66, and other monitoring 67 devices. The control electronics 30 may include microprocessor controls, with manual or pre-programmed functions (with or without feedback control) to activate parts of particular the devices for process variation, time and sequence. The device contains plural sensors 61, 62, 63 for detecting and measuring harmful substances, including but not limited to pathogens such as bacteria, viruses, protozoa, yeast, mold, spores, pesticides, smoke and poisonous gases. The sensors 61, 62, 63 may be located inside or outside of the chamber and may be recorded attended or unattended by a computer or microprocessor. The system 8 also preferably contains sensors for process conditions such as temperature, humidity, chemistry or gas species. The sensors are capable of interacting with device components activating the process manually or automatically through control electronics. The sensors are capable of activating pre-programmed processes according to the detection. The sensors are also capable of in situ feedback control of process parameters, such as activation of different components, process duration, process parameters and control electronics.

In operation, a contaminated article A is placed in processing chamber 20 of the system 8, and the system 8 is switched on. The electrodes 11 in the main processing chamber 10 generates electric and magnetic fields, ultraviolet radiation, and ozone gas, any of which can kill bacteria, viruses, spores, and other airborne pathogens, by disrupting the cell walls or protein coats. At the same time, ionized air, ozone or ultraviolet energy react with chemical contaminants either on the surface of the article or in the surrounding air inside the main processing chamber 10, to oxidize or reduce the substance into a harmless or less harmful state. The article A is left in the main processing chamber 10 for a period of time sufficient to kill all pathogens and to neutralize, degrade or decompose other toxic substances, compounds, gases and the like. The post-processing chamber 20 includes one or more fine grain passive filters 21, activated charcoal, or electrostatic filters to remove pathogens from the air therein. The air, when moved from the main processing chamber to the post-processing chamber gets neutralized, and then returned to the environment.

Thus, it can be seen that the decontamination system of the present invention presents several advantages over existing purification systems. First, it avoids use of radioactive substances to destroy pathogens and the like, and therefore can be used for household articles without physically harming or altering them, or exposing the user to radiation. For example, the system can eliminate germs, pesticides, toxins, mold on food, utensils, tools, floors, carpets, toys, people, and clothing, as well as household, office or personal items, without using gamma ray, electron beam, or x-ray processes, which are harmful to humans and unsuitable for household use.

It will be appreciated that various changes in the details, materials, and arrangements of the parts that have been described and illustrated in order to explain the nature of this invention may be made by those skilled in the art without departing from the spirit of the present invention, the scope of which is limited only by the following claims.

I claim:

1. An apparatus for removing airborne pathogens and toxic substances from a surface of an article or a volume of air, comprising:
    a main processing chamber having a door for ingress to and egress from the main processing chamber, at least two electrodes for generating current to react with pathogens or toxic substances;
    a post processing chamber comprising at least one filter for removing or absorbing airborne particulates and pathogens, and including low voltage electrodes to neutralize charges in air transmitted from the main processing chamber;
    a shutter between the main processing chamber and the post processing chamber for preventing ultraviolet light from entering the post processing chamber from the main processing chamber; and
    a fan for moving fluid from the main processing chamber to the post processing chamber.

2. An apparatus in accordance with claim 1, additionally comprising an ultraviolet light source comprising the at least two electrodes in a sealed or unsealed tube containing mercury.

3. An apparatus in accordance with claim 1, wherein the main processing chamber has a container therein to hold one or more articles for cleaning.

4. An apparatus in accordance with claim 3, wherein the articles are tools, utensils, toys, furniture, or food items, and the electrodes generate ozone.

5. An apparatus in accordance with claim 3, wherein the pathogens are bacteria, viruses, spores, and where the toxin is an insecticide, pesticide, or poison.

6. An apparatus in accordance with claim 1, additionally comprising a vent for releasing air from inside the post processing chamber.

7. An apparatus in accordance with claim 1, additionally comprising an inlet fan to draw air from outside the apparatus into the main processing chamber for cleaning.

8. An apparatus in accordance with claim 7, wherein the inlet fan includes a passive filter for removing airborne pathogens and toxins therefrom.

9. An apparatus in accordance with claim 7, wherein the inlet fan has a hose attached thereto, to create suction through the hose.

10. An apparatus in accordance with claim 6, additionally comprising a closable vent in the main processing chamber to release reactive air from the main processing chamber to a location outside the main processing chamber.

11. An apparatus in accordance with claim 1, additionally comprising at least one sensor located in the main processing chamber and a controller, responsive to the at least one sensor, for regulating process conditions in the main processing chamber.

12. An apparatus in accordance with claim 11, additionally comprising at least one other sensor located in the post processing chamber and a controller, responsive to the at least one other sensor, for regulating process conditions in the post processing chamber.

13. A process for removing airborne pathogens and toxic substances from a surface of an article or a volume of air, the process comprising:
    introducing the article or volume of air into a main processing zone having at least two high voltage electrodes;
    exposing the article or volume of air to an electric and magnetic field created by the high voltage electrodes in the main processing zone for a period of time sufficient to kill pathogens, including bacteria, viruses, and spores, and to neutralize toxic substances or poisons on the article or in the volume of air;
    removing air from the main processing zone to a post processing zone, filtering the air to remove any pathogens or toxic substances contained therein, and exposing the air to low voltage electrodes to neutralize electric charges contained in the air; and
    expelling the air from the post processing zone.

14. A process in accordance with claim 13, additionally comprising an ozone source and an ultraviolet light source, and wherein the ozone and ultraviolet light activate air and water contained in the main processing zone to create activated air and water for destroying pathogens and neutralizing toxic substances.

15. A process in accordance with claim 13, wherein the main processing zone is separated from the post processing zone by a shutter which prevents passage of ultraviolet light and ozone from the main processing zone to the post processing zone.

16. A process in accordance with claim 13, wherein the post processing zone also has filters to remove or neutralize toxic fluids contained in the air.

* * * * *